United States Patent
Smith (10) Patent No.: US 10,952,897 B1
(45) Date of Patent: Mar. 23, 2021

(54) EYE IMPLANT DEVICES AND METHOD AND DEVICE FOR IMPLANTING SUCH DEVICES FOR TREATMENT OF GLAUCOMA

(71) Applicant: S. Gregory Smith, Wilmington, DE (US)

(72) Inventor: S. Gregory Smith, Wilmington, DE (US)

( * ) Notice: Subject to any disclaimer, the term of this patent is extended or adjusted under 35 U.S.C. 154(b) by 196 days.

(21) Appl. No.: 14/705,687

(22) Filed: May 6, 2015

(51) Int. Cl.
*A61F 9/007* (2006.01)
*A61M 5/20* (2006.01)
*A61M 27/00* (2006.01)
*A61F 9/008* (2006.01)

(52) U.S. Cl.
CPC ...... *A61F 9/00781* (2013.01); *A61F 9/00825* (2013.01); *A61M 5/2053* (2013.01); *A61M 27/002* (2013.01); *A61F 2210/0004* (2013.01); *A61F 2210/0076* (2013.01)

(58) Field of Classification Search
CPC .......................... A61F 9/0781; A61M 27/002
See application file for complete search history.

(56) References Cited

U.S. PATENT DOCUMENTS

| | | | | |
|---|---|---|---|---|
| 6,007,511 A | * | 12/1999 | Prywes | A61F 9/00781 604/9 |
| 7,354,416 B2 | * | 4/2008 | Quiroz-Mercado | A61F 9/00781 604/264 |
| 7,488,303 B1 | * | 2/2009 | Haffner | A61F 9/00781 604/521 |
| 8,852,136 B2 | * | 10/2014 | Horvath | A61F 9/00781 604/8 |
| 2007/0112355 A1 | * | 5/2007 | Salahieh | A61F 2/2418 606/108 |
| 2008/0228127 A1 | * | 9/2008 | Burns | A61F 9/00781 604/9 |
| 2014/0066833 A1 | * | 3/2014 | Yaron | A61F 9/00781 604/9 |

* cited by examiner

*Primary Examiner* — Leslie R Deak
(74) *Attorney, Agent, or Firm* — Andrew L. Salvatore, Esquire (57) ABSTRACT

The present invention provides a method of relieving intraocular pressure by inserting a drainage device into the sclera near the trabecular meshwork from a remote location. The path of insertion is made from a corneal incision and avoids contact with the conjunctiva and tenons tissue. The drainage device comprises a tube like structure and may contain a barb at one end to secure the drainage device. A delivery device may be used to insert the drainage device. The delivery device may be inserted through a corneal incision and directed to the desired area for insertion in to the sclera. The delivery device may then be activated to shoot the drainage device into the sclera to promote increased drainage of aqueous humor and reduce the build up of intraocular pressure.

10 Claims, 10 Drawing Sheets

*Fig. 15*

EYE IMPLANT DEVICES AND METHOD AND DEVICE FOR IMPLANTING SUCH DEVICES FOR TREATMENT OF GLAUCOMA

BACKGROUND OF THE INVENTION

This invention relates to the drainage of aqueous humor from eyes in the course of relieving eye disorders. Specifically, the invention relates to an implant which, when permanently affixed to or implanted in a specific area of the eye, will provide such drainage efficiently, for longer periods than heretofore accomplished, and, in short, will provide relief and prevent, or at least postpone, the adverse ultimate effects of glaucoma. The present invention also relates to a method for treating glaucoma, a method for inserting the implant, and a surgical device for inserting the implant.

The eyeball is composed of three basic layers: (1) the sclera; (2) the middle layer or choroid; and (3) the retina. The sclera 10 is the outer layer of the eyeball. It consists of tough, white tissue consisting of meshwork fibers that serves as the supporting framework of the eye. At the front of the eye, the sclera is continuous with the clear, transparent cornea 20 through which light enters the eye. The clarity of the cornea is maintained by the delicate layer of cells on the posterior side thereof, called the endothelium 30. If a foreign material, such as plastic, metal, hydrogen, silicon, etc., touches the endothelium, these cells will die. However, because of the nature of the endothelium cells, which are designed to pump fluid out of the cornea, the death of these cells can impair the vision of the eye. The corneal endothelial cells have tight junctions between them so that fluid will not leak into the cornea and thus need to be pumped out. Should an endothelial cell die, the adjacent cells will expand their size and grow together to reform the tight junction to effect a seal. When such a cell dies, other endothelial cells will migrate and expand into the area previously occupied by the dead cell. A device or other foreign object placed into the trabecular meshwork area of the anterior chamber of the eye should be less than 20 microns in external diameter to avoid touching the corneal endothelium. If the device touches the endothelium, progressive endothelial cell loss will occur, causing the cornea to cloud, causing loss of vision and ultimately for the need for a corneal transplantation. Behind the cornea is a small space, the anterior chamber, which contains a clear watery fluid called the aqueous humor.

The middle layer is composed of three parts: (1) the choroid; (2) the ciliary body 310; and (3) the iris 40. The choroid lies behind and to the sides of the eyeball making up about 80% of the middle layer. It contains most of the blood vessels that nourish the eye.

Toward the front of the eyeball, the choroid becomes the ciliary body or muscle 310. This ciliary body is connected by fibers to the lens 50, keeping the lens in place and controlling its shape. At the very front, the middle layer becomes the iris, a thin curtain of tissue in front of the lens. A round opening in the iris, whose size is controlled by muscles in the iris, is called the pupil 60.

In simple terms, the cornea refracts light through the anterior chamber 70 and then through the pupil, the entrance aperture of the eye to the lens. The lens serves to focus the refracted light through the vitreous chamber 80 containing the vitreous humor onto the retina, the rear surface of the eye.

Figure 1:
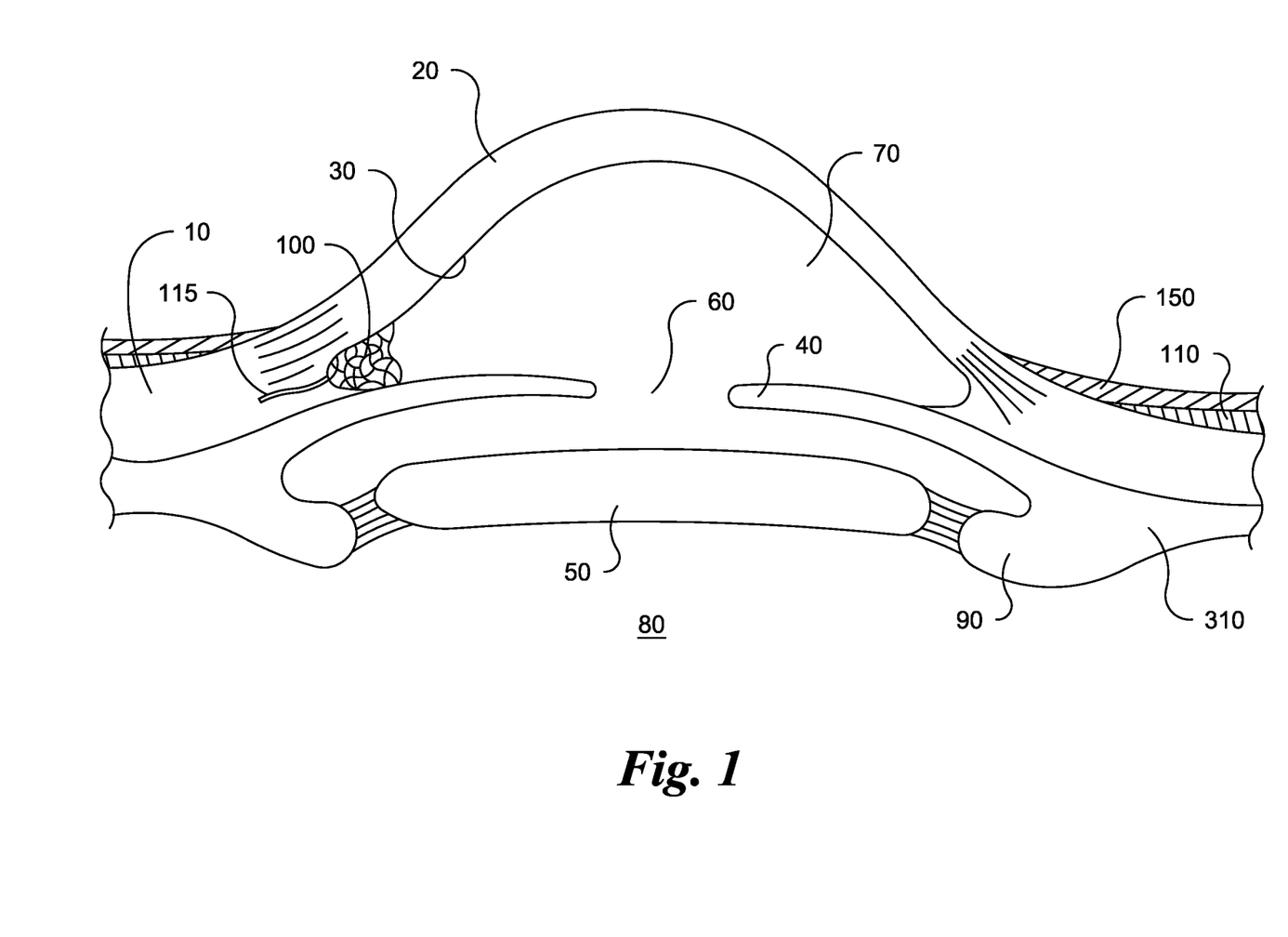
FIG. 1 shows a cross sectional view of an eye.
Figure 2:
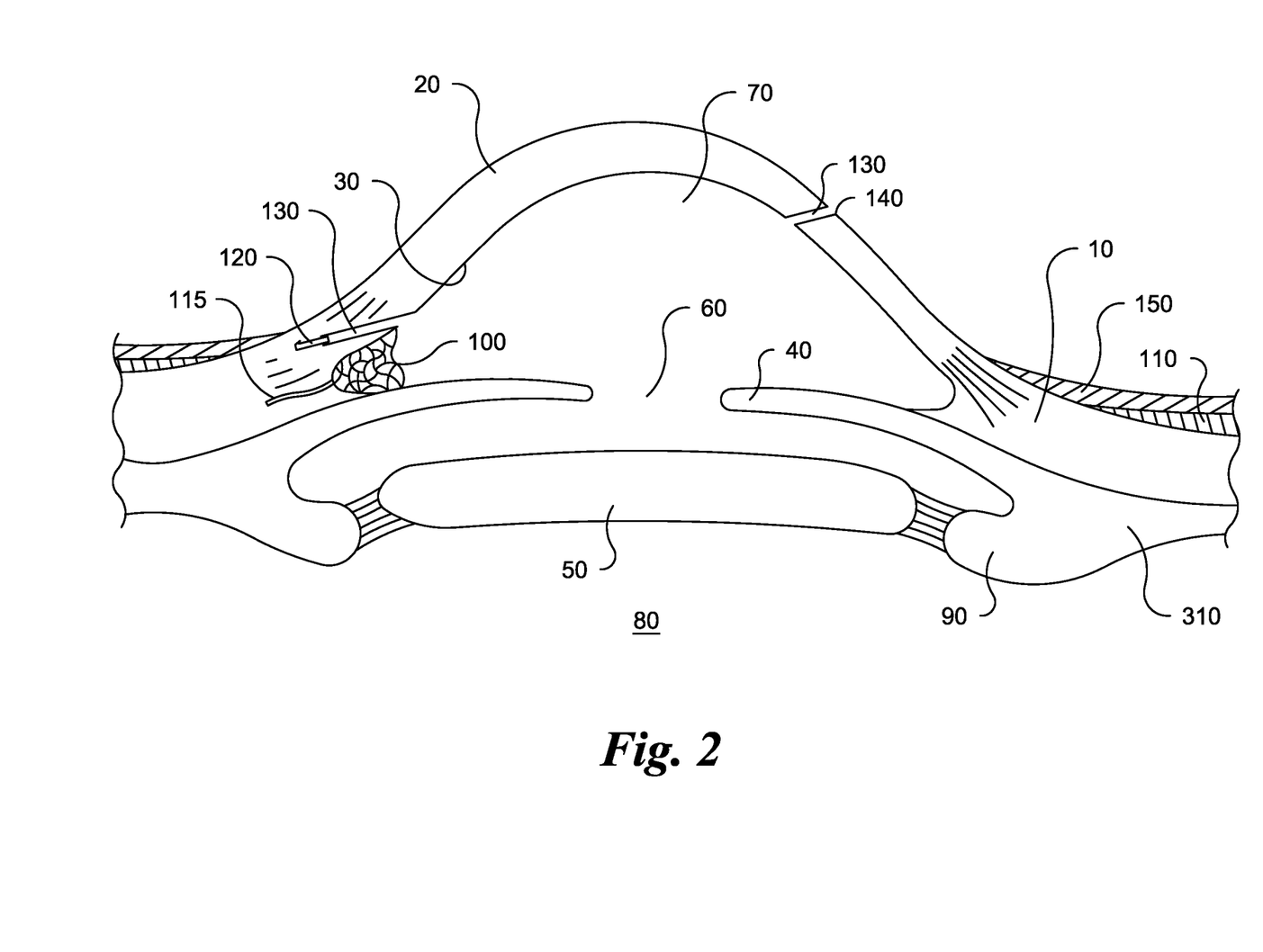
FIG. 2 shows a cross sectional view of an eye with drainage device according to the invention and path of incision.
Figure 3:
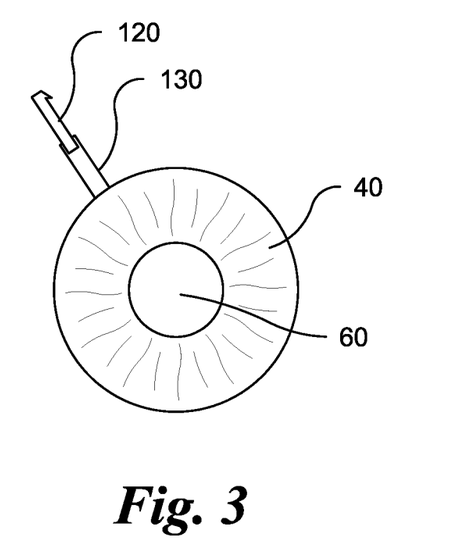
FIG. 3 shows a front elevational view of an eye with drainage device according to the invention and path of incision.

As shown in FIGS. 1-2, normally the fluid within the eye, the aqueous humor, is produced by the ciliary body 90 and migrates through the pupil into the anterior chamber, the small space behind the cornea. From this chamber, the liquid migrates through the trabecular meshwork 100 through Schlemm's canal 115 and into the aqueous veins which form fluid collection channels beneath the conjunctiva 150, the latter covering the front of the eyeball except for the cornea.

When the aqueous migration, described above, is insufficient to relieve the build-up of intra-ocular pressure, glaucoma results. This pressure build-up is usually thought to be due to one or more obstructions in the trabecular meshwork through drainage areas behind the trabecular meshwork which can also impede flow of fluid out of the eye. Unless controlled, the high pressures associated with glaucoma ultimately leads to permanent damage of the optic nerve, the nerve formed from the sensitive fibers of the retina.

The prior art shows many implantable devices and methods of implanting them, but the majority violate the wall of the sclera adjacent to the vascular tissue of the conjunctiva. Such violation causes stimulation of vascular tissue. The sclera does not heal itself, it heals by secondary intention, the process by which blood vessels and connective tissue from the conjunctiva or tenons tissue will migrate into a wound in the sclera. The majority of the prior art also discloses methods and devices that violate the corneal endothelium.

The prior art disclosed an approach to avoid the problem of fluid pressure buildup that involved implanting a device in the sclera. It was noted in surgical studies that the intraocular pressure would drop significantly with the use of this type of device but that over time some eyes would have a rise in intraocular pressure corresponding to a clinical trapping of the aqueous fluid around the implant in the sclera. The sclera is a non-reactive tissue; it only heals when vascular tissue from above or below grows into it. The sclera is also composed of a meshwork of fibrous tissue with passageways or spaces as large as 150 microns. The present invention provides an improved insertable device and a method of inserting such a device into the sclera without causing the conjunctiva to heal and thus block the fluid egress created by the device.

The object of the present invention is to provide a device that can be implanted permanently, simply and effectively to permit substantially normal migration of fluid out of the anterior chamber of the eye and, thus, avoid the abnormal build-up of intra-ocular pressure. Another object is to provide the implant in a manner that will also avoid excessive migration of fluid that would lead to collapse of the anterior chamber with its accompanying complications.

Another object of the present invention is to provide a device and method of implanting the device that eliminates the problem of healing of the conjunctiva and tenon's tissue. Another object of the invention is to provide an implant or insertable device and a method of inserting the implant or device that prevents it from contacting the corneal endothelium.

SUMMARY OF THE INVENTION

The present invention provides a method for provides a method of relieving intraocular pressure in an eye, the eye comprising a cornea, conjunctiva, tenons, vascular tissue and sclera, the method consisting of inserting a glaucoma drainage device without making an incision in the conjunctiva or tenons. The method comprises making a hole or opening in the cornea at a site remote from the conjunctiva and tenons tissue and remote from the area where the drainage device is to be inserted. The delivery device is then inserted across the anterior chamber to the area of the trabecular meshwork. The device is then delivered through the cornea/trabecular meshwork area into the sclera. The drainage device comprises a tube like structure to permit drainage of pressure from a build up of aqueous humor. The drainage device may contain a barb like structure at one end to prevent the device from becoming dislodged once inserted in the sclera. To insert the device, the device may be inserted into a delivery device, in particular, a delivery device which shoots the drainage device into the sclera at the desired location in the sclera. The delivery device is then positioned adjacent to the desired location for insertion of the drainage device. The delivery device then shoots the drainage device into the sclera in a dart like manner.

The invention also comprises a drainage device which, when inserted into the sclera, permits the drainage of excess aqueous humor from within the anterior chamber of the eye and provides a remedy for the elevated pressure of glaucoma. The drainage device comprises a tube like structure through which aqueous humor is drained from the anterior chamber to the fluid collection channels beneath the conjunctiva. The drainage device may be conical in shape, being smaller in diameter at one end than the other. The drainage device may also be a mesh tube or drain or any other device that allows the flow of aqueous humor. The drainage device may contain a barb like structure at one end to secure the drainage device within the sclera and prevent the migration of the drainage device back in the direction of the anterior chamber.

The invention can also include a delivery device for inserting the drainage device. The delivery device may include a pressure shaft into which the drainage device is inserted. When sufficient pressure builds within the pressure shaft, the drainage device is expelled into the sclera at the desired location. The devices to deliver the drainage device can be pneumatic, hydraulic, mechanical, or manual or others, the principle being to deliver the implant into the tissue. A simple manual device would be a plunger similar to a syringe or piston whereby the operator pushes the plunger to push the device into the scleral tissue. Another embodiment would consist of a system of gears which could be driven by a motor or by manually pulling a trigger. The gears would advance the plunger to deliver the device into the tissues. Alternately, a spring may advance the plunger to deliver the device, and the delivery device may be activated by a foot switch. Still another embodiment would involve a pressurized system. Ideally the pressure would be calibrated to deliver the device a certain distance into the tissue; i.e. a force of 20 mm of mercury would drive it 4 mm into sclera, 30 mm of mercury would drive it 6 mm into the sclera. These numbers would have to be tested and verified in actual tissue to confirm, they are hypothetical and given only for example here. A pump would generate this pressure and when the device is where the surgeon would like it to be a footswitch or trigger would be activated. This would release the appropriate amount of force into the tube holding the drainage device and the drainage device would be delivered into the sclera tissue. Air or balanced salt solution would be permissible and the best to be delivered into the eye, other biocompatible fluids could be used. The pump itself would use hydraulic fluids or air.

DETAILED DESCRIPTION OF THE INVENTION

The present invention provides a device and a method for reducing intraocular pressure that overcomes the problems associated with prior devices and methods. The description below illustrates possible embodiments of the present invention and are in no way meant to be limiting. Other embodiments within the scope of the invention will be clear to those skilled in the art.

The subject invention involves a new method of treating glaucoma to insert one or more drainage devices into a location remote from the conjunctiva and tenons tissue into the sclera to facilitate drainage of aqueous humor from the eye. The incision may be remote from the area where the drainage device is to be inserted. The invention also comprises the drainage device and the delivery device, in particular, the delivery device for inserting the drainage device. The surgery for reducing intraocular pressure in the prior art typically involved inserting an implantable device through the conjunctiva. Often such surgery also encroached on the corneal endothelium.

Previous devices have been implanted in schlemms canal through the anterior chamber as well as through the tenons and conjunctiva. Schlemms canal is approximately 50 microns in size, a circular tube. It is located circumferentially around the eye at the limbus, the area of the eye where sclera and iris meet. Technically these surgeries are difficult. When accessing schlemms canal from the anterior chamber the device must be inserted to access the canal which is perpendicular to the line of approach. Some reduction of pressure occurs but the most used of these devices must be done in combination with cataract surgery. This new device improves these limitations by allowing a direct line of approach since the device will ignore the location of schlemms canal as it goes past schlemms canal to access the multiple openings in the sclera, some as large as 150 microns. It thereby accesses larger openings and the surgeon is not required to make an angular maneuver. In going past schlemms canal the device may go through the canal on its way to the sclera but does not have to necessarily be inserted completely past the area of the canal.

According to the method of the invention, the drainage device should be inserted in the area at or near the area at which the trabecular meshwork exists to allow the best access to the sclera. Using this method, the insertion surgery can now be performed in a completely novel way. Instead of a large 8 mm or greater incision into the conjunctival tissue and further incisions into the sclera which would allow the ingrowths of vascular tissue (such tissue would seal off the openings in the sclera wall and block the egress of fluid through the sclera and therefore raise the intraocular pressure "IOP"), an incision 130 is made into the nonvascular cornea at a remote location 140 and entry into the sclera is made from the anterior chamber thus avoiding the tenons tissues and conjunctiva. Thus, the conjunctiva is not incised and the wall of the sclera is not opened (in a preferred embodiment of the method of the present invention). It is important that the path of insertion of the implant and the implant itself do not touch the areas of the eye with blood vessels, so that no healing occurs to block the flow of aqueous humor through the implant.

The scleral tissue consists of a meshwork of fibers and is not capable of healing on its own. When I performed surgery with implants in the sclera I noted an initial dramatic response, the iop starting at 70 and dropping to 10 mm hg. This lasted three months and then the iop elevated to 35. Clinically the sclera over the device became transparent as it filled with fluid but the healing of the conjunctiva and tenons had sealed than fluid in, thwarting the full filtration of the fluid. I then began to search for a method of implanting a device without incising these vascular tissues which causes a healing response.

According to the method of the present invention, the healing response of the conjunctiva 150 and tenon's tissue 110 is not stimulated because there is no incision in these tissues and no fibrovascular growth can access into the sclera since there is no incision in the sclera in an area where vascular tissue exists. As is seen in the methods of the prior art, such ingrowths of vascular tissue would cancel the effects of the surgery, causing any drainage device implanted to fail by blocking the channels or pores with vascular tissue. In the subject invention, by accessing the site of implantation of the drainage device through the cornea and from the anterior chamber, the conjunctiva and tenon's tissue is not affected, and there is no ingrowth of vascular tissue to reduce drainage of aqueous humor from the anterior chamber. Once fluid is delivered to the sclera it is able to pass through the meshwork of fibers and eventually drain into the episcleral vessels which have a pressure of about 9 mm of hg. In this way hypotony or low Intraocular pressure is avoided. Furthermore since this scleral fiber meshwork has multiple openings as large as 150 microns there is a much greater capability to drain fluid than that of schlemms canal which has a single opening of 50 microns.

The device of the invention, which allows drainage of aqueous humor and reduces increased pressure in the eye, comprises a drainage device 120. The drainage device 120 is generally in the form of a tubular structure, in a preferred embodiment, approximately 3 mm in overall length. However, the drainage device may range generally from 0.1 mm to 8 mm depending on the size of the area of insertion. The drainage device has to be long enough to reach the scleral fibers behind the trabecular meshwork/schlemms canal area. In a preferred embodiment, the drainage device may also be approximately 0.3 mm in outside diameter but may range generally from 0.1 mm to 1 mm in outside diameter depending on the size of the area of insertion.

Figure 4:
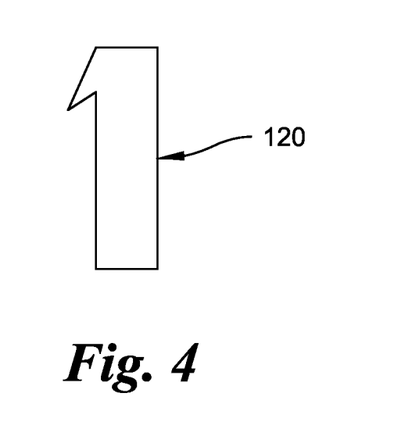
FIG. 4 shows a front elevational view of an embodiment of a drainage device according to the invention.
Figure 5:
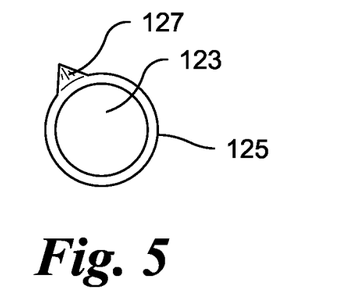
FIG. 5 shows a top plan view of an embodiment of a drainage device according to the invention.
Figure 6:
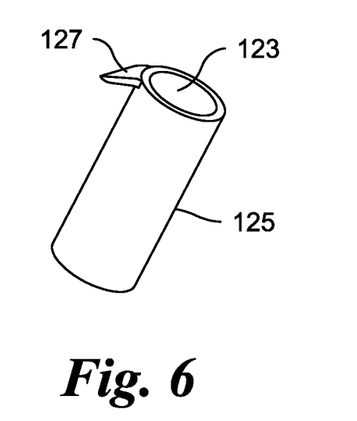
FIG. 6 shows a perspective view of an embodiment of a drainage device according to the invention.

The drainage device may be inserted into the sclera, preferably near the trabecular meshwork, as shown in FIG. 2. As shown in FIGS. 4-6, the tubular portion 123 of the drainage device allows aqueous humor to drain from the anterior chamber, through the tubular portion of the drainage device, and into the sclera. The tubular portion has a tubular wall 125 which encloses a space through which the aqueous humor may pass. The drainage device may also contain a barb 127 at one end or both ends to hold the drainage device in place once inserted and to prevent the drainage device from migrating back toward the anterior chamber. More than one barb may be used to anchor the drainage device into position. The barb may be at varying locations, the purpose being to secure the device.

Figure 7:
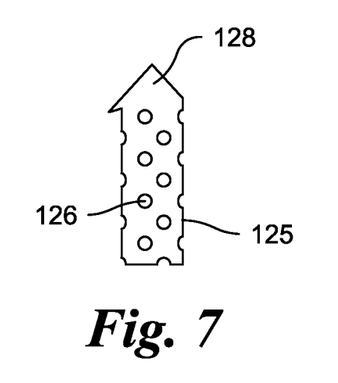
FIG. 7 shows a front elevational view of an embodiment of a drainage device according to the invention.
Figure 8:
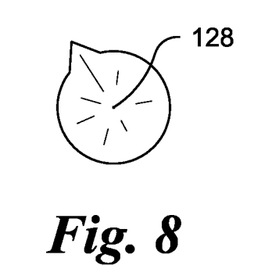
FIG. 8 shows a top plan view of an embodiment of a drainage device according to the invention.
Figure 9:
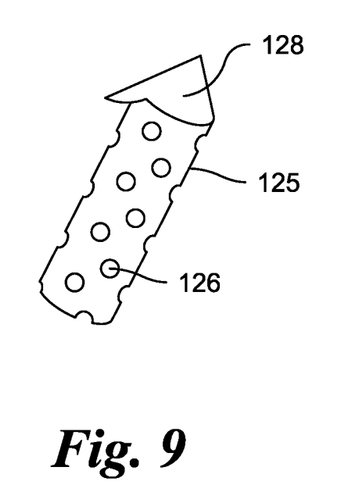
FIG. 9 shows a perspective view of an embodiment of a drainage device according to the invention.

In another embodiment of the drainage device, as shown in FIGS. 7-8, the tubular wall 125 may contain holes or perforations 126 to permit the drainage of aqueous humor from the anterior chamber, through the tubular portion, through the holes 126 and into the sclera. In this the embodiment, the tubular portion of the drainage device is closed at one end to form a closed point end 128. Utilizing this embodiment, the drainage device may be inserted into the sclera with a delivery device, and the closed point end better enables the drainage device to push into the sclera into proper position.

The drainage device may be constructed from a wide variety of materials, preferably those that are biocompatible. Biocompatible materials that may be used include metals or plastics which are biocompatible. In general, the material would be one that has been approved for use in the human body for any surgery. Some examples would be silicone, pmma, acrylics, titanium, titanium with heparin coating, nickel titanium alloys, gold, polyamides, bovine or porcine gelatin crosslinked with glutaraldehyde, stainless steel, polystyrene-block-isobutylene-block-styrene or SIBS, polyurethane, to name a few. The drainage device may also be biodegradable if it is desired that the drainage device only remain in place for a period of time.

Figure 10:
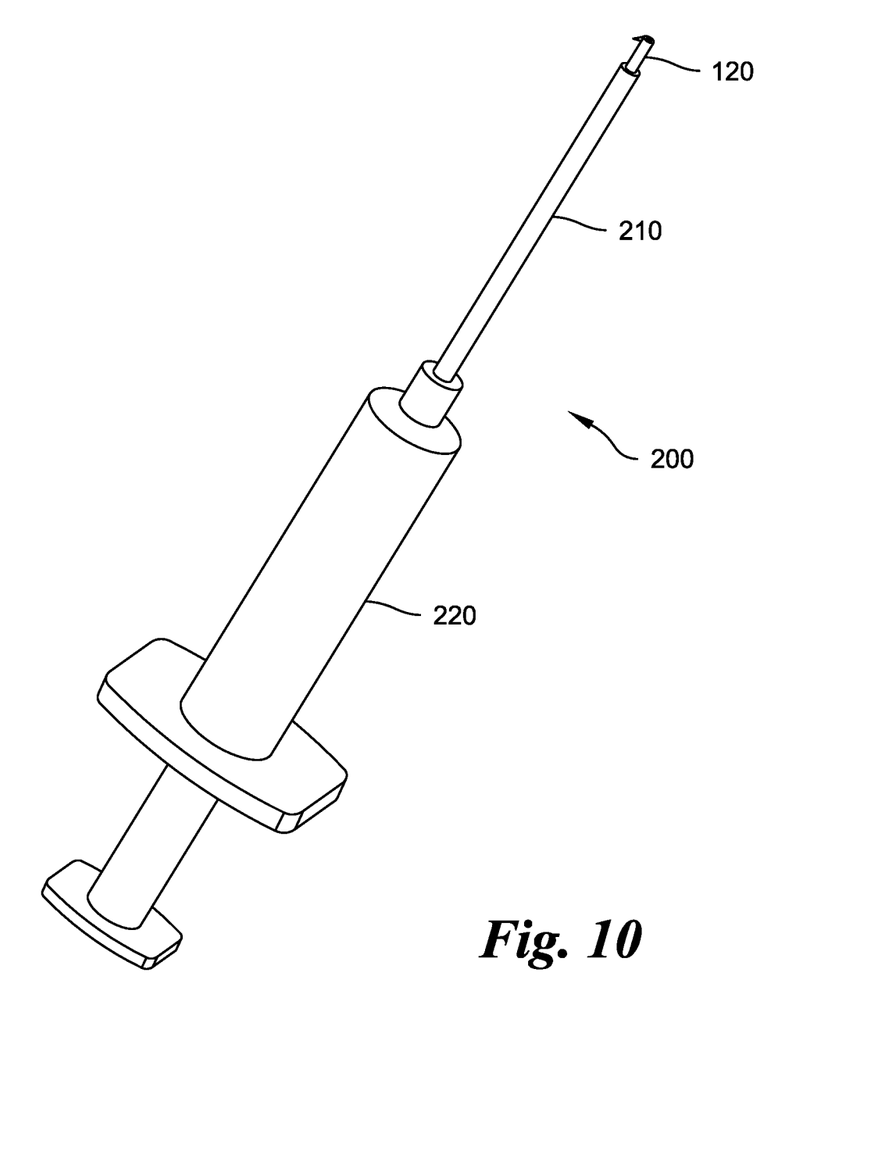
FIG. 10 shows a perspective view of a delivery device using a syringe for implantation of the drainage device according to the invention.
Figure 11:
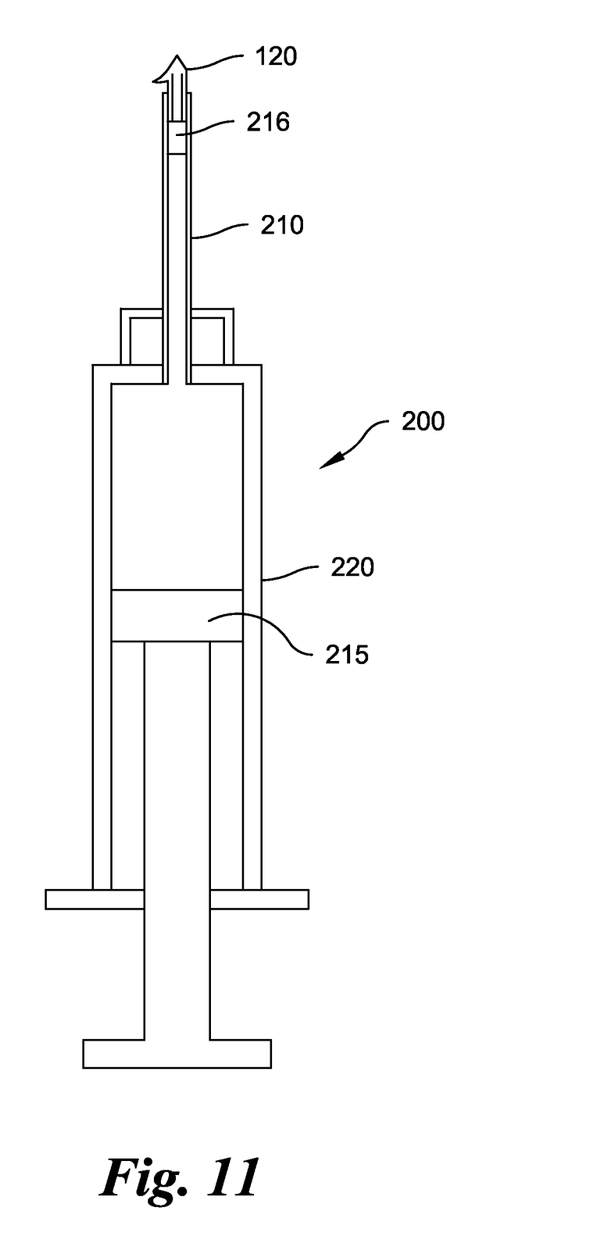
FIG. 11 shows a cross sectional view of the delivery device of FIG. 10 according to the invention.

The drainage device may be inserted into the sclera by means of a delivery device, a delivery device 200. In its simplest form, as shown in FIGS. 10 and 11, the delivery device comprises a pressure shaft 210 into which the drainage device 120 may be inserted at one end of the pressure shaft. The pressure shaft has a tubular wall enclosing a space. The outside diameter of the drainage device should be roughly equal to the interior diameter of the pressure shaft so that the drainage device is held securely within the pressure shaft until a sufficient amount of pressure is generated to expel the drainage device from the delivery device. In a preferred embodiment, the inside diameter of the tubular wall of the pressure shaft is between 0.1 mm and 1 mm, but preferably approximately 0.3 mm, such that the drainage device forms a tight pressure fit when inserted into the pressure shaft.

A means of generating pressure may be secured to the pressure shaft at the opposite end to create pressure within the pressure shaft to expel the drainage device. The means for generating pressure may be comprised of a syringe or piston 220 which when depressed creates pressure within the pressure shaft to expel the drainage device from the pressure shaft. The syringe may be a standard syringe with a tubular enclosed wall and a plunger 215 tightly fitted within the tubular wall and slideable with the tubular wall to force air or liquid toward the drainage device. A second plunger 216 may be positioned tightly within the pressure shaft and slideable within the pressure shaft. The second plunger may be adjacent to the drainage device to prevent the escape of air or liquid when the syringe is depressed which allows pressure to build within the pressure shaft to expel the drainage device.

Figure 12:
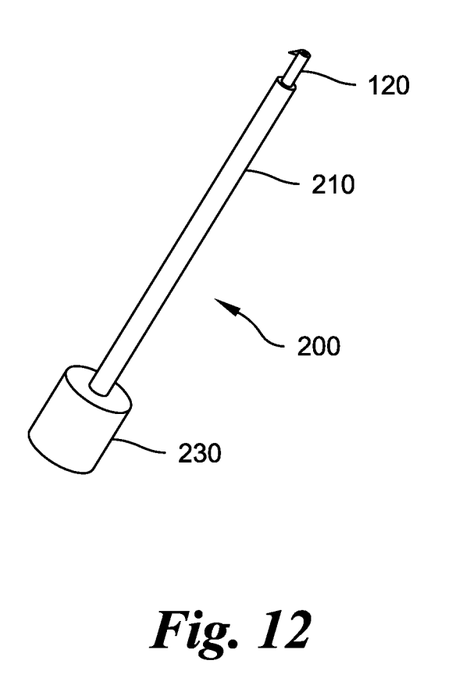
FIG. 12 shows a perspective view of a delivery device using a compressed air capsule for implantation of the drainage device according to the invention.

As shown in FIG. 12, the means for generating pressure may be comprised of a compressed air or fluid capsule 230 with a trigger mechanism to release an appropriate amount of air or fluid into the pressure shaft.

Figure 13:
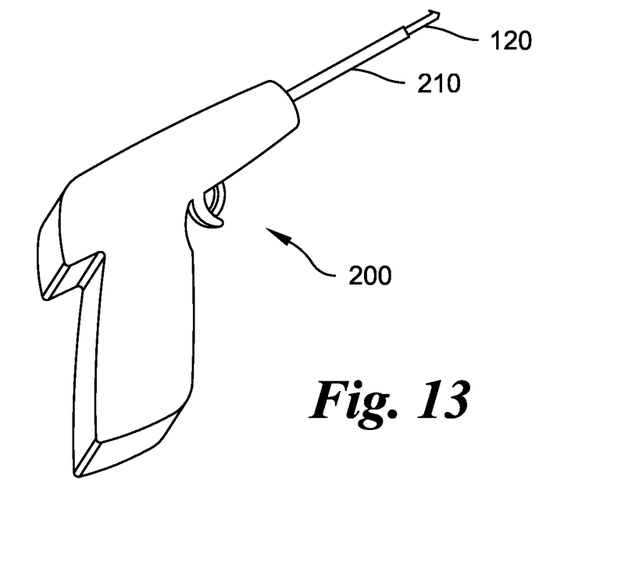
FIG. 13 shows a perspective view of a delivery device using a mechanical spring for implantation of the drainage device according to the invention.
Figure 14:
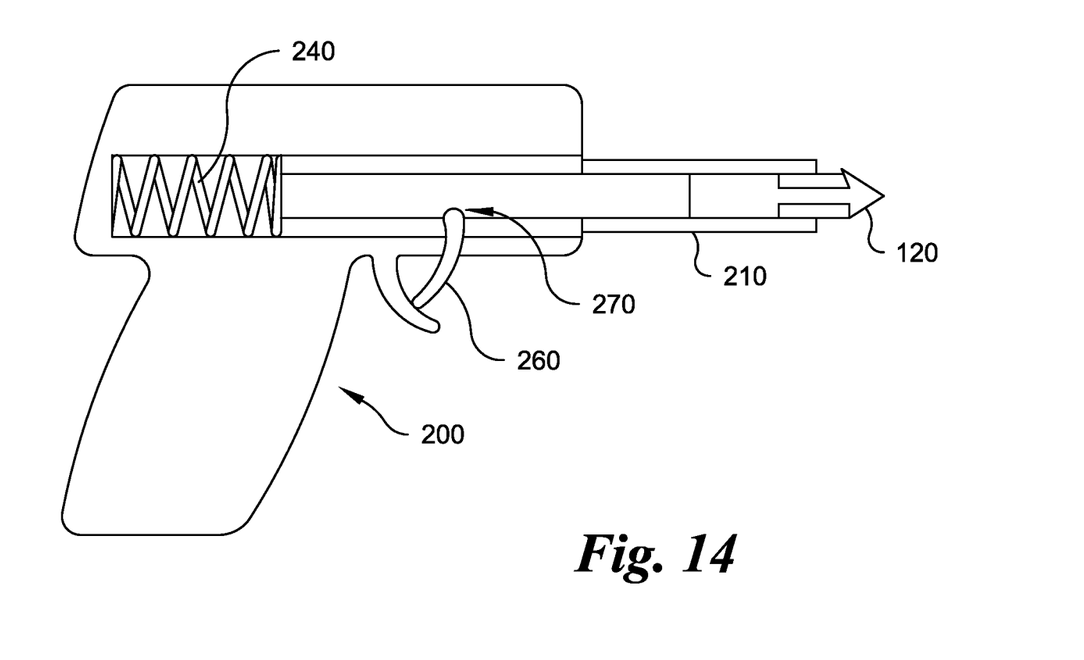
FIG. 14 shows a cross sectional view of the delivery device of FIG. 13 according to the invention.

As shown in FIGS. 13 and 14, the delivery device may generate pressure to expel the drainage device by means of a spring 240. Pressure rod 250 and spring 240 may be positioned within a housing. Pressure rod 250 may be inserted to compress the spring 240 and held in place with a trigger mechanism 260. A notch 270 engages the trigger 260 to hold pressure rod in position when the spring is compressed. When the trigger is pulled, pressure rod is forced into the pressure shaft 210 toward drainage device 120 to force the drainage device from the pressure shaft.

Figure 15:
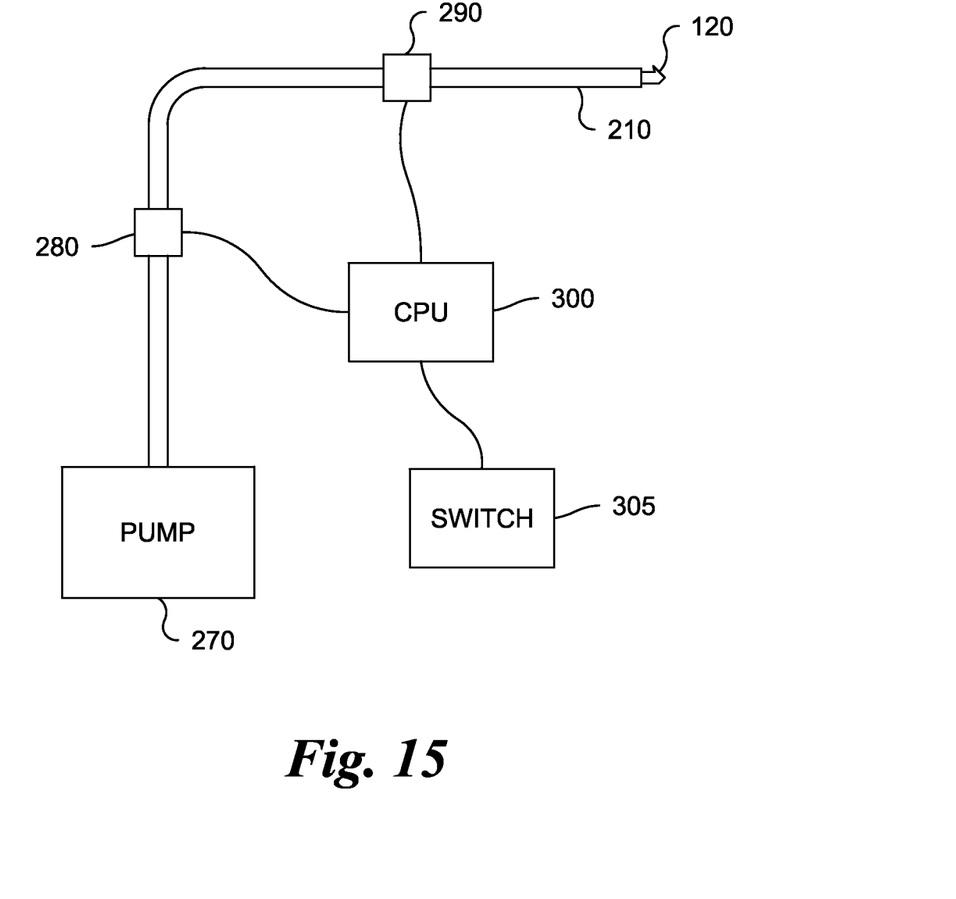
FIG. 15 shows an elevational view of a delivery device using a pump for implantation of the drainage device according to the invention.

As shown in FIG. 15, a pump 270 may generate the pressure to expel drainage device 120 from the pressure shaft 210. The pump may be connected to the pressure shaft by connecting tubes or hoses. A pressure regulator 280 may be positioned between the pump and the pressure shaft and may regulate the amount of pressure within the system until pressure is to be released to expel the drainage device. The pressure regulator may consist of sensors, mircoprocessors and the like to monitor the pressure and signal the pump when more pressure is needed. A valve 290 may be positioned between the pump and the pressure shaft such that when activated, the valve may be opened to release air or liquid into the pressure shaft to force the drainage device from the pressure shaft. A central processing unit (CPU) 300 may be electronically connected to the pressure regulator and may control the amount of pressure building within the system by controlling the pressure regulator to prevent excess buildup of pressure. The CPU may also be electronically connected to the valve and may control when pressure is released from the system into the pressure shaft to expel the drainage device. A switch 305 may be electronically connected to the CPU to control with the valve is opened to release pressure in the system and expel the drainage device. The switch may be a foot switch or other switch which serves the needs of the operator of the delivery device.

A further advantage of this surgery compared to traditional glaucoma surgery is that it can be performed with topical anesthesia. The patient is brought into the operating room and the eye is anesthetized with topical lidocaine or equivalent. The operating microscope is brought into view and the site for the implant is determined. A stab incision into the cornea is made roughly 180 degrees from the selected site using a laser or a blade or drill. Unpreserved lidocaine 1% is irrigated into the anterior chamber. A gonio lens of the Koeppe type is placed on the cornea. This allows the surgeon to view the anterior chamber angle through the operating microscope. Once this view of the trabecular meshwork is obtained a viscoelastic component such as hyaluronic acid Amvisc® or other is injected into the anterior chamber to push the iris back and protect the cornea. A drill is then placed through the stab incision and then introduced across the anterior chamber to the trabecular meshwork area. A laser or blade may also be used. The drill is approximately 0.2 mm in diameter. It can extend to a diameter of 0.6 mm as the sclera ranges from 0.7 mm to 1 mm thick in normal eyes. The drill may be used to enter the wall of the sclera to provide an entry point for the drainage device. Care should be taken to direct the drill into the wall of the sclera and not above or below the sclera for this most ideal form of surgery. The operating microscope can be used to obtain a direct view of this area using the Koeppe lens or equivalent. A laser or a blade may be used instead of a drill in a similar manner. An ultrasonic handpiece may also be attached to the drill or laser or blade for creating the opening or passage in the sclera.

The use of real time ultrasonography on the sclera above the area of surgery may also be used. Use of ultrasonography would aid in determining the exact thickness of tissue being removed. Accordingly, an ultrasound transmitting and sensing device may be positioned at or near the end of a drill or blade which will be used to excise sclera from an eye to insert a drainage device or other intraocular pressure relieving device. The user may then transmit and send ultrasound signals to determine the position of objects and devices, including surgical tools, within the sclera. Once positioning of objects in the sclera is determined, the user may cut into the sclera in response to those signals so that a drainage device or other intraocular pressure relieving device may be inserted and avoid cutting into undesired regions within the eye. The use of ultrasonography may also be helpful to use during the drilling maneuver to make a corneal incision to achieve the optimum location.

The drill may then be removed from the incision and the drainage device inserted into the sclera using the delivery device 200. The delivery device, with drainage device inserted, should be inserted into the eye through the corneal opening made by the drill. The delivery device should then be directed through the anterior chamber and positioned near the sclera at the desired point of insertion at incision made by the drill. In a preferred embodiment, the drainage device is positioned within the sclera so that the drainage device does not contact endothelial cells.

If the delivery device is utilizing pressure to expel the drainage device, the means for generating pressure should then apply an appropriate amount of pressure to release the drainage device from the delivery device and shoot it into the sclera. Various embodiments of the delivery device, including those shown in FIGS. 10-15, may be used to expel the drainage device. The drainage device may be inserted fully into the sclera. The drainage device may also be inserted such that the barb end of the drainage device is positioned within the sclera and the opposite end of the drainage device extends from the sclera and into the anterior chamber. Even if a portion of the drainage device extends into the anterior chamber, the drainage device may be positioned so as not to contact corneal endothelial cells which would result in death of those cells. More than one drainage device may be implanted to achieve the desired amount of drainage of aqueous humor.

In this manner, no incision is made in vascular tissue. The cornea has no vessels. The sclera has an occasional vessel which goes through it. The sclera heals only by secondary intention. Since the conjunctiva and tenons tissue have not been violated no blood vessels will grow in from above. Since the ciliary body has not been violated from below, no blood vessels will grow in from this source. There are no blood vessels in the anterior chamber for the normal eye and in all glaucomas except for neovascular glaucoma. The intrascleral drainage device would not fare as well in neovascular glaucoma as the progressive growth of scar tissue (called peripheral anterior synechiae) will close over the sclerostomy (the opening made by the drill or drainage device into the anterior chamber). The drainage device may be recessed behind the opening (sclerostomy). In this situation the drainage device would have to extend into the anterior chamber to make it more difficult for tissue to grow over the opening. It should be noted that it may not be necessary to use a drill to implant the device. The simplest method would be to use a drainage device of sufficient structural stability that could be simply shot (or placed) into the sclera through the general area of the trabecular meshwork. This would involve a corneal incision remote from the implant site, placing a gonio lens or other device for visualization, extending across the anterior chamber with the device and delivery instrument and then implanting the device.

The ability to quickly implant the drainage device, and the ability to implant the drainage device from a remote location bypassing the conjunctiva and tenon's tissue, offers a distinct advantage over the prior art and solves many problems created by the prior art methods and devices. In particular, the subject invention can be implanted so that it does not contact endothelial cells which would cause death of those cells, and the drainage device may be implanted quickly and with minimal surgical intervention. As has been previously shown, the main issues with glaucoma surgery are scarring which blocks the flow of fluid out of the eye and the pressure dropping too low after surgery causing poor vision because the eye cannot maintain its shape. The drainage device addresses both of these as no blood vessels are violated to cause scarring within the sclera, and the sclera itself is porous and drains into the episcleral vessels which have a pressure of about 9 mm of mercury. If the endothelium is a concern and this is the preferred embodiment, the drainage device can be implanted totally within the sclera so that it is recessed and none is exposed to the endothelium. Alternatively, it can be implanted such that a portion protrudes into the anterior chamber. This would provide for greater ease of surgery for most surgeons.

The distinct advantage of the drainage device is that there is no incision in the conjunctiva or tenons tissue while accessing the scleral tissue for drainage. The drill or implant device approaches these tissues from the inside of the eye, and the vascular tissue is located above and below the sclera. This would be visualized directly with the operating microscope. As the drill begins to penetrate, a viscoelastic substance could be then injected through the drilled passageway and move these tissues away from the sclera. The drilling could then be completed and the device inserted. Irrigation or irrigation and aspiration could also be used to remove cut tissue or other material.

The invention has been disclosed in terms of preferred embodiments which fulfill all of the objects of the present invention and overcome the limitations of the prior art. Various changes, modifications, and alterations from the teachings of the present invention may be contemplated by those skilled in the art without departing from the intended spirit and scope thereof. It is intended that the present invention only be limited by the terms of the appended claims.

I claim:

1. A method for inserting a drainage device into an eye to relieve intraocular pressure, the eye comprising at least a cornea, tenons tissue, a lens, anterior chamber, sclera, conjunctiva, trabecular meshwork, schlemms canal, and corneal endothelium, the method comprising:
    determining a site for locating and implanting the drainage device;
    making an incision in the cornea at a remote location;
    inserting a delivery device containing the drainage device into the anterior chamber to the site for implanting the drainage device;
    implanting the drainage device into the sclera by utilizing the delivery device to deliver the drainage device with sufficient force to penetrate into the sclera bypassing the trabecular meshwork and Schlemm's canal, the drainage device having at least one barb and the drainage device providing fluid communication between the anterior chamber and the sclera,
    anchoring of the barb of the drainage device into the sclera, and
    removing the delivery device.

2. A method for inserting a drainage device into an eye to relieve intraocular pressure as in claim 1, after making a corneal incision, further comprising the steps of:
    inserting a drill or laser or blade into the corneal incision across an anterior chamber to the area of the sclera near the trabecular meshwork of the eye in the area located to implant the drainage device;
    creating an opening or passage in the sclera in the area of the trabecular meshwork of the eye with the drill or laser or blade;
    extending the opening or passage into the sclera of the eye;
    removing the drill or laser or blade from the eye.

3. A method for inserting a drainage device into an eye to relieve intraocular pressure as in claim 1, wherein the delivery device uses pressure against the drainage device to shoot the drainage device into the sclera.

4. A method for inserting a drainage device into an eye to relieve intraocular pressure as in claim 1, wherein the delivery device applies air or liquid pressure to expel the drainage device.

5. A method for inserting a drainage device into an eye to relieve intraocular pressure as in claim 1, wherein the delivery device uses the force of a spring to expel the drainage device.

6. A method for inserting a drainage device into an eye to relieve intraocular pressure as in claim 1, wherein the delivery device uses a pump and a central processing unit to regulate air or liquid pressure to expel the drainage device.

7. An implantable pressure relieving drainage device for the treatment of glaucoma comprising
    a tubular portion having an overall length in the range from 0.1 mm to 0.49 mm and having an outside diameter in the range from 0.1 mm to 1 mm and the tubular portion having two ends and a tubular side wall enclosing an interior space, the tubular side wall containing at least one opening, the at least one opening being positioned to be in fluid communication with a sclera of an eye and
    at least one barb connected to the tubular wall at one end, wherein aqueous humor may pass through the at least one opening to reduce pressure within an eye.

8. An implantable pressure relieving device for the treatment of glaucoma as in claim 7 wherein one end of the tubular portion further comprises a closed point end.

9. An implantable pressure relieving drainage device for the treatment of glaucoma as in claim 7 wherein the drainage device is in a conical shape at one end of the tubular portion, the drainage device being smaller in diameter at one end than the other and the tubular wall containing at least one hole.

10. An implantable pressure relieving drainage device for the treatment of glaucoma as in claim 7 wherein the drainage device is a mesh tube or drain that allows the flow of aqueous humor.

* * * * *